United States Patent [19]
Termine et al.

[11] Patent Number: 5,340,934
[45] Date of Patent: Aug. 23, 1994

[54] CDNA SEQUENCES OF HUMAN BONE MATRIX PROTEINS

[75] Inventors: John D. Termine, Bethesda; Marian F. Young, Silver Spring; Larry W. Fisher, Rockville; Pamela G. Robey, Bethesda, all of Md.

[73] Assignee: The United States of Americas as represented by the Secretary of Health & Human Services, Washington, D.C.

[21] Appl. No.: 432,044

[22] Filed: Nov. 3, 1989

[51] Int. Cl.⁵ .................... C07H 17/00; C12N 15/00
[52] U.S. Cl. ................................ 536/23.5; 536/231; 935/60; 935/6; 935/9
[58] Field of Search ............... 436/536, 509, 512, 513, 436/547; 530/350; 536/23.5, 1, 24.31

[56] References Cited

U.S. PATENT DOCUMENTS 4,645,748  2/1987  Hurwitz et al. ..................... 436/509
4,795,804  1/1989  Urist ................................... 530/350

OTHER PUBLICATIONS

Computing generated sequence comparison Registry file No. 141374-20-1.
Fisher, et al., *The Journal of Biological Chemistry*, vol. 264, No. 8, Mar. 15, 1989, pp. 4571-4576.
Lankat-Buttgereit et al. FEBS Lett. 236, 352-356 (1988) Sequ only.
Swaroop et al. Genomics. 2, 37-47 (1988). Sequence only.
Mason, et al. EMBO J. (1986) 5:1465-1472. Sequence only.
Findlay et al. Biochemstry (1988) 27:1483-1489.
Krusius, T. et al. P.N.A.S. (1986) 83:7683-7687. Sequence only.
Day, et al. Biochem. J. 248, 801-805 (1987). Sequence only.
Craig et al. J. Biol. Chem. 264, 9682-9689 (1989). Sequence only.
Kiefer, et al. EMBL entry (1988) Sequence only.
Oldberg et al. J. Biol. Chem. (1988) 263:19430-19432. Sequ. only.
McVey et al. J. Biol. Chem. (1988) 263:11111-11116 Sequence only.
Bolander et al. PNAS 85 2919-2923 (1988). Sequence only.
Biochemical and Biophysical Research Communication, vol. 164, No. 1, issued Oct. 16, 1989, Giri et al. entire article and computer comparison of sequence.
Fisher et al., Deduced protein sequence of bone small proteoglycan I biglycan shows homology with proteoglycan II decorin and several nonconnective tissue proteins in a variety of species, 1989, *J. Biol. Chem.* 264: 4571-4576.
Neame et al., The primary structure of the core protein of the small, leucine-rich proteoglycan (PG I) from bovine articular cartilage, 1989, *J. Biol. Chem.* 264: 8653-8661.
Marcus-Sekura, "Techniques for using antisense oligooxyribonucleotides to study gene expression", *Analytical Biochemistry* 172, 289-295 (1988).
Fisher et al. *The Journal of Biological Chemistry*, vol. 262, No. 20 issue of Jul. 15, 1987, pp. 9702-9708.
*Methods in Enzymology*, Horn et al. "Production of Reagent Antibodies", vol. 70, pp. 104-142, 1980.
Sommer et al. "Minimal homology requirements for PCR primers", *Nucleic Acids Research*, vol. 17, No. 16, pp. 6749, 1989.

*Primary Examiner*—Margaret Parr
*Assistant Examiner*—Bradley L. Sisson
*Attorney, Agent, or Firm*—Townsend and Townsend Khourie and Crew

[57] ABSTRACT

Amino acid and cDNA sequences of a plurality of human bone matrix proteins and their uses have been described.

1 Claim, 17 Drawing Sheets

```
  1  GAGTAGCTGCTTTCGGTCCGCCGGACACCGGACAGATAGACGTCCGGACGGCCCACCA              60

61  CCCCAGCCCGCCAACTAGTCAGCCTGGCCTGCGCCTCCCTCTCCAGTCCATCCGCC              120

121  ATGTGGCCCCTGTGGCGCCTCGTGTCTCTGCTGGCCCTGAGCCAGGCCCTGCCCTTTGAG         180
      M  W  P  L  W  R  L  V  S  L  L  A  L  S  Q  A  L  P  F  E

181  CAGAGAGGCTTCTGGGACTTCACCCTGGACGATGGGCCATTCATGATGAACGATGAGGAA         240
      Q  R  G  F  W  D  F  T  L  D  D  G  P  F  M  M  N  D  E  E

241  GCTTCGGGCGCTGACACCTCAGGCGTCCTGGACCCCGACTCTGTCACACCCACCTACAGC         300
      A  S  G  A  D  T  S  G  V  L  D  P  D  S  V  T  P  T  Y  S

301  GCCATGTGTCCTTTCGGCTGCCACTGCCACCTGCGGGTGGTTCAGTGTCCGACCTGGGT          360
      A  M  C  P  F  G  C  H  C  H  L  R  V  V  Q  C  S  D  L  G

361  CTGAAGTCTGTGCCCAAAGAGATCTCCCCTGACACCACGCTGCTGGACCTGCAGAACAAC         420
      L  K  S  V  P  K  E  I  S  P  D  T  T  L  L  D  L  Q  N  N

421  GACATCTCCGAGCTCCGAAGGATGACTTCAAGGTCTCCAGCACCTCTACGCCCTCGTC          480
      D  I  S  E  L  R  K  D  D  F  K  G  L  Q  H  L  Y  A  L  V

481  CTGGTGAACAACAAGATCTCCAAGATCCATGAGAAGGCCTTTCAGCCCCTACTGCGGAACGTG     540
      L  V  N  N  K  I  S  K  I  H  E  K  A  F  S  P  L  R  N  V

541  CAGAAGCTCTACATCTCCAAGAACCACCTGGTGGAGATCCCGCCAACCTACCAGCTCC         600
      Q  K  L  Y  I  S  K  N  H  L  V  E  I  P  P  N  L  P  S  S

601  CTGGTGGACGTCCGCATCCACGACAACAGGATCCGCAAGGTGCCCAAGGGAGTGTTCAGC       660
      L  V  D  V  R  I  H  D  N  R  I  R  K  V  P  K  G  V  F  S

661  GGGCTCCGGAACATGAACTGCATCGAGATGGGCGGGAACCCACTGGAGAACAGTGGCTTT       720
      G  L  R  N  M  N  C  I  E  M  G  G  N  P  L  E  N  S  G  F
```

*FIG. IA.*

```
721  GAACCTGGAGAGCCTTCGATGGGCCTTCGAAGCTCAACTACCTGCGGATCTCAGAGGCCAAGCTG  780
     E  P  G  A  F  D  G  L  K  L  N  Y  L  R  I  S  E  A  K  L

781  ACTGGCATCCCCAAAGACCTCCCTGAGAACCTGAATGAACTCCACTTAGACCACAACAAA      840
     T  G  I  P  K  D  L  P  E  T  L  N  E  L  H  L  D  H  N  K

841  ATCCAGGCCATCGAACTGGAGGACCTGCTTCGCTACTCCAAGCTGTACAGGCTGGGCCTA      900
     I  Q  A  I  K  L  E  D  L  L  R  Y  S  K  L  Y  R  L  G  L

901  GGCCACAACCAGATCAGGATGATCGAGAACGGGAGCCTGAGCTTCCTGCCCACCCTCCGG      960
     G  H  N  Q  I  R  M  I  E  N  G  S  L  S  F  L  P  T  L  R

961  GAGCTCCACTTGGACAACAACAAGTTGGCCCAGGTGCCCTCAGGGCTCCCAGACCTCAAG      1020
     E  L  H  L  D  N  N  K  L  A  R  V  P  S  G  L  P  D  L  K

1021 CTCCTCCAGGTGGTCTATCTGCACTCCAACAACATCACCAAAGTGGGTGTCAACGACTTC     1080
     L  L  Q  V  V  Y  L  H  S  N  N  I  T  K  V  G  V  N  D  F

1081 TGTCCCATGGGCTTCGGGGTGAAGCGGGCCTACTACAACGGCATCAGCTCTCTTCAACAAC    1140
     C  P  M  G  F  G  V  K  R  A  Y  Y  N  G  I  S  L  F  N  N

1141 CCCGTGCCCTACTGGGAGGTGCAGCCGGCCACTTTCCGCTGCGTCACTGACCGCCTGGCC     1200
     P  V  P  Y  W  E  V  Q  P  A  T  F  R  C  V  T  D  R  L  A

1201 ATCCAGTTTGGCAACTACAAAAAGTAGAGGCAGCTGCAGCCACCGCGGGGCCTCAGTGGG     1260
     I  Q  F  G  N  Y  K  K  *

1261 GGTCTCTGGGGAACACAGCCAGACATCCTGATGGGGAGGCAGAGCCAGGAAGCTAAGCCA     1320

1321 GGGCCCAGCTGCGTCCAACCTGTCCCTCAGGTCCCTGACCCTCAGCTCGATGCCC         1380

1381 CATCACCGCCCTCTCCCTGGCTCCCAGGGTGCAGGTGGGCGCAAGGCCCGGCCCCCATCA    1440

1441 CATGTTCCCTTGGCCTCTCAGAGCTGCCCTGCTCTCCCACCACAGCCACCCAGAGGCACCC   1500

1501 CATGAAGCTTTTTTCTCGTTCACTCCCAAACCCAAGTGTCCAAAGCTCCAGTCCTAGGAG   1560
```

FIG. 1B.

1561 AACAGTCCCTGGGTCAGCAGCCAGGAGGCGGTCCATAAGAATGGGGACAGTGGGCTCTGC 1620
1621 CAGGGCTGCCGGCACCTGTCCAGAACAACATGTTCTGTTCCTCCTCCTCATGCATTTCCAG 1680
1681 CCTTG 1685

FIG. 1C.

```
  1 CTCCTTCTGC TTGCACAAGT TTCCTGGGCT GGACCGTTTC AACAGAGAGG
 51 CTTATTTGAC TTTATGCTAG AAGATGAGGC TTCTGGGATA GGCCCAGAAG
101 TTCCTGATGA CCGCGACTTC GAGCCCCTCC TAGGCCCCAGT GTGCCCCTTC
151 CGCTGTCAAT GCCATCTTCG AGTGGTCCAG TGTTCTGATT TGGGTCTGGA
201 CAAAGTGCCA AAGGATCTTC CCCCTGACAC AACTCTGCTA GACCTGCAAA
251 ACAACAAAAT AACCGAAATC AAAGATGGAG ACTTTAAGAA CCTGAAGAAC
301 CTTCACGCAT TGATTCTCTGT CAACAATAAA ATTAGCAAAG TTAGTCCTGG
351 AGCATTTACA CCTTTGGTGA AGTTGGAACG ACTTTATCTG TCCAAGAATC
401 AGCTGAAGGA ATTGCCAGAA AAAATGCCCA AAACTCTTCA GGAGCTGCGT
451 GCCCATGAGA ATGAGATCAC CAAAGTGCGA AAAGTTACTT TCAATGACT
501 GAACCAGATG ATTGTCATAG AACTGGGCAC CAATCCGCTG AAGAGCTCAG
551 GAATTGAAAA TGGGGCTTTC CAGGGAATGA CAGCATTCCT CTACATCCGC
601 ATTGCTGATA CCAATATCAC CAGCATTCCT CAAGGTCTTC CTCCTTCCCT
651 TACGGAATTA CATCTTGATG GCAACAAAAT CAGCAGAGTT GATGCAGCTA
701 GCCTGAAAGG ACTGAATAAT TTGGCTAAGT TGGGATTGAG TTTCAACAGC
751 ATCTCTCGCTG TTGACAATGG CTCTCTGGCC AACACGCCTC ATCTGAGGGA
801 GCTTCACTTG GACAACAACA AGCTTACCAG AGTACCTGGT GGGCTGGCAG
851 AGCATAAGTA CATCCAGGTT GTCTACCTTC ATAACAACAA TATCTCTGTA
                             FIG. 2A.
```

```
 901 GTTGGATCAA GTGACTTCTG CCCACCTGGA CACAACACCA AAAGGCTTC
 951 TTATTCGGGT GTGAGTCTTT TCAGCAACCC GGTCCAGTAC TGGGAGATAC
1001 AGCCATCCAC CTTCAGATGT GTCTACGTGC GCTCTGCCAT TCAACTCGGA
1051 AACTATAAGT AATTCTCAAG AAAGCCCTCA TTTTTATAAC CTGGCAAAAT
1101 CTTGTTAATG TCATTGCTAA AAAATAAATA AAAGCTAGAT ACTGGAAACC
1151 TAACTGCAAT GTGGATGTTT TACCCACATG ACTTATTATG CATAAAGCCA
1201 AATTTCCAGT TTAAGTAATT GCCTACAATA AAAAGAAATT TTGCCTGCCA
1251 TTTTCAGAAT CATCTTTTGA AGCTTTCTGT TGATGTTAAC TGAGCTACTA
1301 GAGATATTCT TATTTCACTA AATGTAAAAT TTGGAGTAAA TATATATGTC
1351 AATATTTAGT AAAGCTTTTC TTTTTTAATT TCCAGGAAAA AATAAAAAGA
1402 GTATGAGTCT TCTGTAATTC ATTGAGCAGT TAGCTCATTT GAGATAAAGT
1451 CAAATGCCAA ACACTAGCTC TGTATTAATC CCCATCATTA CTGGTAAAGC
1501 CTCATTTGAA TGTGTGAATT CAATACAGGC TATGTAAAAT TTTTACTAAT
1551 GTCATTATTT TGAAAAAATA AATTTAAAAA TACATTCAAA ATT

1 LLLLAQVSWA GPFQQRGLFD FMLEDEASGI GPEVPDDRDF EPSLGPVCPF
 51 RCQCHLRVVQ CSDLGLDKVP KDLPPDTTLL DLQNNKITEI KDGDFKNLKN
101 LHALILVNNK ISKVSPGAFT PLVKLERLYL SKNQLKELPE KMPKTLQELR
```

FIG. 2B.

```
151 AHENEITKVR KVTFNGLNQM IVIELGTNPL KSSGIENGAF QGMKKLSYIR
201 IADTNITSIP QGLPPSLTEL HLDGNKISRV DAASLKGLNN LAKLGLSFNS
251 ISAVDNGSLA NTPHLRELHL DNNKLTRVPG GLAEHKYIQV VYLHNNNISV
301 VGSSDFCPPG HNTKKASYSG VSLFSNPVQY WEIQPSTFRC VYVRSAIQLG
351 NYK*
```

FIG. 2C.

```
  1       GAG GCA GCA GCA GGA GGC AGA GAC AGC ATC GTC GGG ACC AGA CTC GTC TCA GGC

61       CAG TTG CAG CCT TCT CAG CCA AAC GCC GAC CAA GGA AAA CTC ACT ACC ATG AGA ATT GCA
                                                                      Met Arg Ile Ala

121       GTG ATT TGC TTT TGC CTC CTA GGC ATC ACC TGT GCC ATA CCA GTT AAA CAG GCT GAT TCT
  4       Val Ile Cys Phe Cys Leu Leu Gly Ile Thr Cys Ala Ile Pro Val Lys Gln Ala Asp Ser

181       GGA AGT TCT GAG GAA AAG CAG CTT TAC AAC AAA TAC CCA GAT GCT GTG GCC ACA TGG CTA
 25       Gly Ser Ser Glu Glu Lys Gln Leu Tyr Asn Lys Tyr Pro Asp Ala Val Ala Thr Trp Leu

241       AAC CCT GAC CCA TCT CAG AAG CAG AAT CTC CTA GCC CCA CAG ACC CTT CCA AGT AAG TCC
 45       Asn Pro Asp Pro Ser Gln Lys Gln Asn Leu Leu Ala Pro Gln Thr Leu Pro Ser Lys Ser

301       AAC GAA AGC CAT GAC CAC ATG GAT GAT ATG GAT GAT GAA GAT GAT GAC CAT GTG GAC
 65       Asn Glu Ser His Asp His Met Asp Asp Met Asp Asp Glu Asp Asp Asp His Val Asp

361       AGC CAG GAC TCC ATT GAC TCG AAC GAC TCT GAT GAT GTA GAT GAC ACT GAT GAT TCT CAC
 85       Ser Gln Asp Ser Ile Asp Ser Asn Asp Ser Asp Asp Val Asp Asp Thr Asp Asp Ser His
```

```
421  CAG TCT GAT GAG TCT CAC CAT TCT GAT GAA TCT GAT TTT CCC ACG
105  Gln Ser Asp Glu Ser His His Ser Asp Glu Ser Asp Phe Pro Thr

480  GAC CTG CCA GCA ACC GAA GTT TTC ACT CCA GTT GTC CCC ACT GAT GGC
125  Asp Leu Pro Ala Thr Glu Val Phe Thr Pro Val Val Pro Thr Asp Gly

540  CGA GGT GAT AGT GTG GTT TAT GGA CTG AGG TCA AAA TCT CGC AGA CCT GAC
145  Arg Gly Asp Ser Val Val Tyr Gly Leu Arg Ser Lys Ser Arg Arg Pro Asp

601  ATC CAG TAC CCT GAT GCT ACA GAC GAG GAC ATC ACC TCA CAC ATG GAA GAG TTG
165  Ile Gln Tyr Pro Asp Ala Thr Asp Glu Asp Ile Thr Ser His Met Glu Glu Leu

661  AAT GGT GCA TAC AAG GCC ATC CCC GTT GCC CAG GAC CTG AAC GCG CCT TCT GAT TGG GAC
185  Asn Gly Ala Tyr Lys Ala Ile Pro Val Ala Gln Asp Leu Asn Ala Pro Ser Asp Trp Asp

721  AGC CGT GGG AAG GAC AGT TAT GAA ACG AGT CAG CTG GAT GAC CAG AGT GCT GAA ACC CAC
205  Ser Arg Gly Lys Asp Ser Tyr Glu Thr Ser Gln Leu Asp Asp Gln Ser Ala Glu Thr His

781  AGC CAC AAG CAG TCC AGA TTA TAT AAG CGG AAA GCC AAT GAT GAG AGC AAT GAG CAT TCC
225  Ser His Lys Gln Ser Arg Leu Tyr Lys Arg Lys Ala Asn Asp Glu Ser Asn Glu His Ser
```

```
901  CAC AGC CAT GAA GAT ATG CTG GTT GTA GAC CCC AAA AGT AAG GAA GAT AAA CAC CTG
265  His Ser His Glu Asp Met Leu Val Val Asp Pro Lys Ser Lys Glu Asp Lys His Leu

961  AAA TTT CGT ATT TCT CAT GAA TTA GAT AGT GCA TCT TCT GAG GTC AAT TAA AAG GAG AAA
285  Lys Phe Arg Ile Ser His Glu Leu Asp Ser Ala Ser Ser Glu Val Asn

1021 AAA TAC AAT TTC TCA CTT TGC ATT TAG TCA AAA GAA AAA ATG CTT TAT AGC AAA ATG AAA

1081 GAG AAC ATG AAA TGC TTC TTT CTC AGT TTA TTG GTT GAA TGT GTA TCT ATT TGA GTC TGG

1141 AAA TAA CTA ATG TGT TTG ATA ATT AGT TTA GTT TGT GGC TTC ATG GAA ACT CCC TGT AAA

1201 CAA AAG CTT CAG GGT TAT GTC TAT GTT CAT TCT ATA GAA ATG CAA ACT ATC ACT GTA

1261 TTT TAA TAT TTG TTA TTC TCT CAT GAA TAG AAA TTT ATG TAG AAG CAA ACA AAA TAC TTT

1321 TAC CCA CTT AAA AAG AGA ATA TAA CAT TTT ATG TCA CTA TAA TCT TTT GTT TTT TAA GTT
```

FIG. 3C.

1381 AGT GTA TAT TTT GTT GTG GTA ATT ATC TTT TGT GGT GTG AAT AAA TCT TTT ATC TTG AAT GTA

1441 ATA AGA AAA AAA AAA AAA AAA AAA AAA AAA AAA AAA AAA AAA AAA AAA AAA AAA AAA AA

FIG. 3D.

|  |  |  |  |  |  |
|---|---|---|---|---|---|
| 1 | CCTGCTCAGC | ATCACAGGGG | ACTGGACTCT | TCTCGCCGCC | GCAGACCAAG |
| 51 | GAAAAATCAT | TACCATGAGA | ATTGCAGTGA | TTTGCTTCTG | CCTCTTGGGC |
| 101 | ATTGCCTCCG | CCCTTCCAGT | TAAACCGACC | AGTTCTGGCA | GCTCTGAGGA |
| 151 | AAAGCAGCTT | AACAACAAAT | ACCCAGATGC | TGTAGCCATA | TGGCTAAAXX |
| 201 | CTGACCCATC | TCAGAAGCAG | ACTTTCCTAA | CACCACAGAA | TTCTGTGTCC |
| 251 | TCTGAGGAAA | CTGATGACAA | CAAACAAAAT | ACCCTCCCAA | GTAAGTCCAA |
| 301 | TGAAAGCCCT | GAGCAAACAG | ACGATCTAGA | TGACGATGAT | GATAACAGCC |
| 351 | AGGACGTCAA | CTCTAATGAC | TCCGACGACG | CTGAAACCAC | TGATGACCCT |
| 401 | GACCATTCCG | ACGAGTCTCA | CCATTCTGAT | GAATCTGATG | AAGTTGATTT |
| 451 | TCCCACTGAT | ATTCCAACAA | TCGCAGTTTT | CACTCCGTTT | ATCCCTACGG |
| 501 | AAAGGCGAAA | TGATGGCCGA | GGTGATAGTG | TGGCTTACGG | ACTGAAGTCA |
| 551 | AGATCTAAGA | AGTTCCGCCG | ATCTAACGTT | CAGAGTCCAG | ATGCCACAGA |
| 601 | GGAGGACTTC | ACATCACACA | TAGAGAGTGA | GGAGATGCAT | GACGCACCTA |
| 651 | AGAAGACGAG | TCAGCTGACT | GACCACAGCA | AGGAAACCAA | CAGTAGCGAG |
| 701 | CTTTCCAAAG | AACTCACGCC | AAAGGCCAAG | GATAAGAACA | AGCATTCCAA |
| 751 | TCTGATTGAG | AGTCAGGAAA | ATTCCAAACT | CAGCCAAGAA | TTCCATAGCC |
| 801 | TTGAAGACAA | GCTAGACCTA | GATCATAAGA | GTGAAGAAGA | CAAACACCTG |
| 851 | AAAATTCGTA | TTTCTCATGA | ATTAGATAGT | GCCTCTTCTG | AGGTCAATTG |

FIG. 4A.

```
 901  AAAGGAGAAA ATACAATTTC TTACTTTGCT TTTAGTAAAA CGAAAGGAT
 951  ACATTAAAGC AGGGTGGGAG ACAATATGAA ATGCATATTT CTCAGCTTAG
1001  TTGGTGAATG TATATGTGTG TAGATCTGGA AACAGATCAT GTTTTTGATC
1051  ATTAGTTTAA TGTGTGGCTT CATGGTAACA CCCTTCTAAA CTAAAAGCTT
1101  CAGAGTTTAG TCTATGTTCT TTCCACATAC AAAATGCAAA CCATCACAGC
1151  ATTTTAATGT TTGCTACCCT TTTAGGAATA GAAATTCATG TAGAAGCAAA
1201  CAAATACTG TTACACACTT TTAAGAAAGA ATATAAAATT TGATGTCACT
1251  ATGATCTTTT GTTTTTTAAA TTAGTATATA TTTTGTTGTG ATTATTTTT
1301  CTGTGTGTGAA TAAATCTTTT ATCTTGAATG TGAAAAAAAA AAAAAAAAA
1351  AAAAAA
```

MRIAVICFC LLGIASALPV KPTSSGSSEE KQLNNKYPDA VAIWLXXDPS QKQTFLTPQN
SVSSEETDDN KQNTLPSKSN ESPEQTDDLD DDDDNSQDVN SNDSDDAETT DDPDHSDESH
HSDESDEVDF PTDIPTIAVF TPFIPTESAN DGRGDSVAYG LKSRSKKFRR SNVQSPDATE
EDFTSHIESE EMHDAPKKTS QLTDHSKETN SSELSKELTP KAKDKNKHSN LIESQENSKL
SQEFHSLEDK LDLDHKSEED KHLKIRISHE LDSASSEVN*

```
GAA GGA AAT GAA AAC GAA AGC GAA GCA GAA GTG GAT GAA AAC GAA CAA GGC ATA AAC    602
Glu Gly Asn Glu Asn Glu Ser Glu Ala Glu Val Asp Glu Asn Glu Gln Gly Ile Asn

GGC ACC AGT ACC AAC AGC GAG ACA GCA GAA AAC GGC AGC GGA GAC AAT                662
Gly Thr Ser Thr Asn Ser Glu Thr Ala Glu Asn Gly Ser Gly Asp Asn

GGA GAA GGG GAA GAA GAA ACT GTC AAT GCA GAA GCC ACA GGC ACC                    722
Gly Glu Gly Glu Glu Glu Thr Val Asn Ala Glu Ala Thr Gly Thr

GGA GGG CAG GGC AAG ACC TCG AAG ACA ACC CCA AAT GGT GGG TTT GAA CCT            782
Gly Gly Gln Gly Lys Thr Ser Lys Thr Thr Pro Asn Gly Gly Phe Glu Pro

ACA ACC CCA CAA GTC TAT AGA ACC ACT TCC CCA TTT GGG AAA ACC ACC GTT            842
Thr Thr Pro Gln Val Tyr Arg Thr Thr Ser Pro Phe Gly Lys Thr Thr Val

GAA TAC GAG GGG GAG TAC ACG GGC GTC AAT GAC TAC AAT GGA TAT GAA ATC            902
Glu Tyr Glu Gly Glu Tyr Thr Gly Val Asn Asp Tyr Asn Gly Tyr Glu Ile

TAT GAA AGT GAG AAC GGG GAA CCT [CGT GGG GAC] AAT TAC CGA GCC TAT GAA GAT GAG TAC  962
Tyr Glu Ser Glu Asn Gly Glu Pro [Arg Gly Asp] Asn Tyr Arg Ala Tyr Glu Asp Glu Tyr

AGC TAC TTT AAA GGA CAA GGC TAT GAT GGT TAT GAT GGC TAC AAT TAC CAC CAC CAG   1022
Ser Tyr Phe Lys Gly Gln Gly Tyr Asp Gly Tyr Asp Gly Tyr Asn Tyr His His Gln

TGA AGC TCC AGC CTG   1037
End
```

```
  1  CCA CTA AGG GTT CCC AGC ACC ATG AGG GCC TGG ATC TTC TTT CTC TGC CTG GCC GGG    60
                             Met Arg Ala Trp Ile Phe Phe Leu Cys Leu Ala Gly
                                                              10

61  AGG GCC TTG GCA GCC CCT CAG CAA GAA GCC CTG CCT GAT GAG ACA GAG GTG GTG GAA GAA   120
     Arg Ala Leu Ala Ala Pro Gln Gln Glu Ala Leu Pro Asp Glu Thr Glu Val Val Glu Glu
                               20                              30

121  ACT GTG GCA GAG GTG ACT GTA TCT GTG GGA GCT AAT CCT GTC CAG GTA GAA GTA GGA   180
     Thr Val Ala Glu Val Thr Val Ser Val Gly Ala Asn Pro Val Gln Val Glu Val Gly
                           40                              50

181  GAA TTT GAT GAT GGT GCA GGA GAG GTG GTG GCG GAA CCC TGC CAG   240
     Glu Phe Asp Asp Gly Ala Gly Glu Val Val Ala Glu Pro Cys Gln
                           60                              70

241  AAC CAC CAC TGC AAA GGC AAG GTG TGC GAG CTG GAT GAG AAC AAC ACC CCC ATG TGC   300
     Asn His His Cys Lys Gly Lys Val Cys Glu Leu Asp Glu Asn Asn Thr Pro Met Cys
                           80                              90

301  GTG TGC CAG GAC CCC ACC AGC TGC CCA GCC CCC ATT GGC GAG TTT GAG AAG GTG TGC AGC   360
     Val Cys Gln Asp Pro Thr Ser Cys Pro Ala Pro Ile Gly Glu Phe Glu Lys Val Cys Ser
                           100                             110
```

FIG. 6A.

```
361  AAT GAC AAC AAG ACC TTC GAC TCT TCC TGC CAC TTC TTT GCC ACA AAG TGC ACC CTG GAG  420
     Asn Asp Asn Lys Thr Phe Asp Ser Ser Cys His Phe Phe Ala Thr Lys Cys Thr Leu Glu
                             120                             130

421  GGC ACC AAG GGC CAC AAG CTC CAC CTG GAC TAC ATC GGG CCT TGC AAA TAC ATC CCC      480
     Gly Thr Lys Gly His Lys Leu His Leu Asp Tyr Ile Gly Pro Cys Lys Tyr Ile Pro
                             140                             150

481  CCT TGC CTG GAC TCT GAG TTC CCC CTG ATG CGG GAC AAC AAC CTT CTG ACT GAG AAG AAC  540
     Pro Cys Leu Asp Ser Glu Phe Pro Leu Met Arg Asp Asn Asn Leu Leu Thr Glu Lys Asn
                             160                             170

541  GTC CTG ACC CTG TAT GAG TAT GAG AAG CGC CTG GAG GCA GGA GAC CAC CCC GTG           600
     Val Leu Thr Leu Tyr Glu Tyr Glu Lys Arg Leu Glu Ala Gly Asp His Pro Val
                             180                             190

601  CTG CGG GTG AAG AAG ATC CAT GAG AAT GAG GCA GGA GAC CAC CCC                      660
     Leu Arg Val Lys Lys Ile His Glu Asn Glu Ala Gly Asp His Pro
                             200                             210

661  GAG CTG CGG GCC CGG GAC TTC GAG AAG AAC TAT AAC ATG TAC ATC TTC CCT GTA CAC TGG  720
     Glu Leu Arg Ala Arg Asp Phe Glu Lys Asn Tyr Asn Met Tyr Ile Phe Pro Val His Trp
                             220                             230
```

FIG. 6B.

```
721  CAG TTC GGC CAG CTG GAC CAG CAC CCC ATT GAC GGG TAC CTC TCC CAC ACC GAG CTG GCT
     Gln Phe Gly Gln Leu Asp Gln His Pro Ile Asp Gly Tyr Leu Ser His Thr Glu Leu Ala   780
                          240                         250
781  CCA CTG CGT GCT CCC CTC ATC CCC ATG GAG CAT TGC ACC CGC TTT TTC GAG ACC TGT
     Pro Leu Arg Ala Pro Leu Ile Pro Met Glu His Cys Thr Arg Phe Phe Glu Thr Cys        840
                          260                         270
841  GAC CTG GAC AAT GAC AAG TAC ATC GCC CTG GAT GAG TGG GCC GGC TGC TTC GGC ATC AAG
     Asp Leu Asp Asn Asp Lys Tyr Ile Ala Leu Asp Glu Trp Ala Gly Cys Phe Gly Ile Lys   900
                          280                         290
901  CAG AAG GAT ATC GAC AAG GAT CTT GTG ATC TAA                                        933
     Gln Lys Asp Ile Asp Lys Asp Leu Val Ile  *
                          300
```

FIG. 6C.

CDNA SEQUENCES OF HUMAN BONE MATRIX PROTEINS

The present invention is related generally to providing cDNA sequences of proteins. More particularly, the present invention is related to providing cDNA sequences as well as sense and anti-sense RNA and DNA sequences and the deduced amino acid sequences of a plurality of human bone matrix proteins, specific antisera and various applications thereof.

BACKGROUND OF THE INVENTION

Certain bone and connective tissue disease processes are detectable by monitoring the level of certain macromolecules in the serum. An example is serum osteocalcin, the levels of which reflect bone turnover. However, heretofore, only a limited number of such macromolecules were known to be related to bone and connective tissue diseases. The macromolecules cited herein comprise the majority (70% of the noncollagenous proteins in the human skeleton) that are truly of bone cell origin, that is the cDNA sequences were derived from screening of normal human bone cell cDNA libraries, and not from cDNA libraries of cells or tissues of other non-bone types, or of transformed cells. The levels in tissues or bodily fluids, such as serum, plasma, crevicular fluid, amniot fluid, urine, etc., of these molecules or their metabolites reflect normal bone metabolism. A shift in those levels from the normal values would be indicative of skeletal and/or connective tissue disease states.

SUMMARY OF THE INVENTION

It is, therefore, an object of the present invention to provide specific cDNA and deduced protein sequences which are diagnostic of such human diseases as osteoporosis, osteo/rheumatold arthritis, Paget's disease, atherosclerosis, periodontal disease and the like.

It is another object of the present invention to provide novel probes (sense and anti-sense RNA and DNA derived from the cDNA sequence), antibodies and bioassays for monitoring the level and distribution of certain human bone matrix proteins in the human body fluids or tissues.

Other objects and advantages will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein:

FIGS. 1-6 show the cDNA and deduced amino acid sequences of human bone biglycan (proteoglycan I), human bone decorin (proteoglycan II), human bone osteopontin Ia and human bone osteopontin II, human bone sialoprotein and human bone osteonectin(ON), respectively.

DETAILED DESCRIPTION OF THE INVENTION

Figure 5A:

The above and various other objects and advantages of the present invention are achieved by utilizing a part or the whole of the cDNA (sense and anti-sense sequences of RNA and DNA derived from the cDNA sequence) and protein sequences shown in FIGS. 1-6. It is noted that given the cDNA and protein sequences shown in FIGS. 1-6, one of ordinary skill in the art can easily prepare or derive specific sequences (sense and anti-sense RNA or DNA) of the cDNA or polypeptides for diagnostic tests or bioassays by standard techniques well known in the art and can be found described in such publication as Maniatis et al (A Laboratory Manual. Cold Spring Harbor Laboratory, Cold Spring Harbor, N.Y., 1982); Davis et al (Basic Methods in Molecular Biology. Elsevier, N.Y., 1986); Ausubel et al (Current Protocols in Molecular Biology. Greene Pub. Assoc. and Wiley Interscience, N.Y., 1987); Koziolkiewicz et al (Chem. Sci. 26: 251–260, 1986); van Regenmortel et al (Laboratory Techniques in Biochemistry and Molecular Biology. Vol 19. Synthetic Polypeptides as Antigens. Amsterdam, Elsevier, 1988); Robey and Fields (Anal. Biochem. 177: 373–377, 1989).

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. It is noted that the methods, materials and examples are only illustrative and not limiting.

The term "substantially pure" as used herein means that the product is as pure as can be obtained by employing conventional isolation and purification techniques known in the art.

MATERIALS AND METHODS

Construction and Screening of a Bone Cell Culture Derived cDNA Library

RNA from primary cultures of adult human bone cells (Gehron Robey et al. Calcif. Tissue Int. 37: 453–460, 1985) was extracted using a guanidine HCl procedure (Adams et al. Proc. Natl. Acad. Sci. U.S.A. 74: 3399–3403, 1977), and poly(A)+ mRNA was isolated by affinity chromatography on oligo(dT)-cellulose (Pharmacia LKB Biotechnology Inc. ). Approximately 20 μg of poly(A)+ was used to construct a gt11 ZAP library ( custom library section of Stratagene Cloning Systems). The amplified cDNA expression library was first screened in *Escherichia coli* BB4 cells as described by Young and Davis (Proc. Natl. Acad. Sci. U.S.A. 80: 1194–1198, 1983) using for example a polyclonal antiserum from a rabbit injected with both human bone PG I and PG II (rabbit LF-5) and a peroxidase-conjugated second antibody made in goat (Kirkegaard and Perry Laboratories). Positive plaques were identified by reaction with $H_2O_2$ and 4-chloro-1-naphthol. Positive clones were rescreened to purity with the same antiserum and then screened again in a second round with antisera made against synthetic peptides corresponding to residues 11–24 of the secreted form of human bone PG I (Fisher et al. J. Biol. Chem. 262: 9702–9708, 1987) or 5–17 of human fibroblast PG II (Krusius and Rouslahti. Proc. Natl. Acad. Sci. U.S.A. 83: 7683–7687, 1986). The synthetic peptides were made on an Applied Biosystems Model 430A peptide synthesizer using t-butoxycarbonyl-protected amino acids and standard reaction conditions suggested by the manufacturer. The peptides were deprotected using anhydrous HF and conjugated either to bovine serum albumin for PG I (LF-15) or to keyhole limpet hemocyanin for PG II (LF-30), respectively, as described (Lindner and Robey. Int. J. Peptide Protein Res. 30: 794–800, 1987). Clones containing cDNA for PG I were found to be missing the start codon of the open reading frame, so the library was rescreened using a 200-bp 5'-EcoRI-BglII fragment labeled with $^{32}$P (Amersham nick translation kit and 3000 Ci/mmol of [$^{32}$P]O$_4$ α-CTP, Du Pont-New England Nuclear ). Prehybridization, high stringency hybridization, washing, and detection on Kodak XOmat AR film were as described (Young et al. Nucleic Acids Res. 12: 4207–4228, 1984). Bone sialoprotein (BSP) and osteopontin (OP) I and II were screened using 32P-labeled rat BSP and OPI, respectively, under moderate stringency conditions ( 60 C.).

DNA Sequence of cDNAs

Purified insert( PGI, PGII, BSP, OPI,OPII and ON) was isolated from plasmid DNA according to the instructions provided by Stratagene Cloning Systems. Briefly, the purified phage vectors containing the cDNAs were used to co-infect a BB4 E. coli strain with R408 helper phage (Stratagene Clong Systems ). The pBluescript plasmid DNA (packaged in M13 or f1 phage particles at this stage) was rescued by infecting and plating fresh bacteria on ampicillin-containing plates. ( Phage in the helper phage preparation were destroyed by heating to 70° C. for 20 min. ) Colonies ( containing the pBluescript plasmid and the cDNA insert) were plucked and grown in a larger scale preparation. As a specific example, PGI cDNA inserts were liberated either with a combination of BamHI and KpnI or XbaI and NaeI (the latter removing only a ~1.0-kbp 5' piece). These large fragments were directionally subcloned in M13mp18 or −19 (Messing et al. Nucleic Acids Res. 9: 309–321, 1981 ) previously restricted with the above enzymes (using SmaI for the NaeI site). Smaller restriction fragments were also made from the XbaI/NaeI fragment using BglII and RSaI and subcloned into appropriately cut M13 vectors. After transformation into JM101 cells, single-stranded DNA from recombinant phage was annealed to either the 17-bp universal primer or the appropriate synthetic oligonucleotide of an internal site (Messing et al. supra) and sequenced using the dideoxy chain termination method (Sanger et al. Proc. Natl. Acad. Sci. U.S.A. 74: 5463–5467, 1977). The SEQUENASE kit (United States Biochemicals ) using both GTP and ITP nucleotide mixes and α-[$^{35}$S]ATP (1110 Ci/mmol, Du Pont-New England Nuclear) were used for the sequencing reactions of PGI and all other clones. The nucleotide sequences were determined by electrophoresis on 6% and 8% polyacrylamide urea gels followed by exposure on X-AR film (Kodak).

Northern Analysis 3.5-μg portions of total RNA from cells in culture (human bone, skin, periodontal ligament, gingiva, bovine bone, chicken embryo fibroblasts, rat osteosarcoma (ROS 17/2), or tissues (bovine: skin, articular cartilage, and cornea; and rat swarm chondrosarcoma) were electrophoresed in 1.2% formaldehyde-agarose gels and transferred to nitrocellulose as described (Maniatis et al. Cloning: A Laboratory Manual, Cold Spring Harbor Laboratory, Cold Spring Harbor, N.Y., 1982). An agarose gel-purified .XbaI-NaeI fragment of PG I (clone P6, included >90% of the coding region of the cDNA but no noncoding regions and corresponded to nucleotides ~180–1130) or PG II (clone P2, entire BamHI/KpnI 1.6-kbp insert) were labeled by nick translation (see above) and hybridized to the RNA bound to the nitrocellulose. Hybridization was carried out at 37° C. in 40% formaldehyde for 16 h, washed, and exposed to x-ray film for 3–6 h as described previously (Shimokawa et al. J. Biol. Chem. 262: 4042–4047, 1987). A blot was probed for PG I mRNA, autoradiographed, stripped of PG I probe by boiling for 5 min in 2×SSC, and 0.1% SDS followed by an ice-cold wash in 2×SSC, and reprobed with the PG II cDNA probe.

Polyacrylamide Gel Electrophoresis and Electroblotting

Polyacrylamide gradient (4–20%) SDS slab gels (160×140×1.5 mm) topped with 3% stacking gel were prepared and electrophoresed as described (Fisher et al. J. Biol. Chem. 258: 6588–6594, 1983). Electrotransfer of core proteins ( in 150 μg dry weight of adolescent monkey bone mineral compartment extract; 200 μg each of 4M guanidine HCl-extracted monkey skin, tendon, cartilage, cornea, or muscle (crude extracts); or 10 μg of purified human bone PG I (Fisher et al. J. Biol. Chem. 262: 9702–9708, 1987) each digested for 1 h at 37° C. with 10 milliunits of chondroitinase ABC (Miles) (Fisher et al, supra) from the SDS gels and onto nitrocellulose was according to the method of Towbin et al (Proc. Natl. Acad. Sci. U.S.A. 76: 4350–4354, 1979). Indirect immunodetection using antisera and conjugated second antibodies was as above.

Probes derived from the cDNA sequence (either sense or anti-sense RNA or DNA, partial or full length), and polyclonal or monoclonal antibodies having specific binding affinity to the amino acid sequences (either synthetic peptide, fusion proteins or full length naturally occuring proteins) of the human bone matrix proteins of the present invention are produced by standard techniques well known in the art. These inventions are used in procedures as noted below.

Immunoassays (RIA and ELISA) with Antibodies Raised Against Either Intact Protein or Synthetic Peptides The invention (synthetic peptide or substantially pure protein, and antibodies raised against either or both) is used in a radioimmunoassay (RIA) to measure levels of the bone matrix proteins or their biosynthetic or degradative products in bodily fluids or tissue extracts (Risteli, et al. In Kuhn, K., Krieg. T. (eds) Connective Tissue: Biological and Clinical Aspects. Munich, Karger. 1986, pp.216–245). First the synthetic peptide or substantially pure protein is used to establish a standard curve by dissolving an accurately measured amount in an appropriate buffer and diluted to yield a series with varying concentrations. The assay tubes (total volume of 200 microliters) for establishing the standard curve contains 100 microliters of the prepared standard ( each tube containing a different amount of polypeptide or protein), 50 microliters of the antibody diluted to an appropriate concentration and 50 microliters of iodinated, or otherwise labeled synthetic peptide or substantially pure protein (~10,000 cpm). The assay tubes for samples to be analyzed contain 50 microliters of buffer, 50 microliters of the analyte, 50 microliters of the diluted antibody and 50 microliters of the labeled peptide or protein. All tubes are incubated overnight at 4° C. Each tube then receives 50 microliters of S. aureus bearing protein A (or any other solid support that binds to antibody) suspended in buffer. The complex is allowed to form during a 2 hour period of tube rocking at 4° C. The immune complexes are then precipitated by centrifugation. The supernate is aspirated and the radioactivity of the pellet determined by scintillation counting. The standard curve is generated by quantitating the amount of radioactivity bound in the immune complex in the presence of increasing amounts of unlabeled peptide or protein. As the amount of unlabeled polypeptide or protein increases, the labeled polypeptide or protein bound decreases since the concentration of antibody is constant. Plotting of the amount of radioactivity vs. the amount of unlabeled polypeptide or protein results in a curve with a linear region. The level of polypeptide or protein in the analytes is determined from the standard curve.

The invention (either polypeptides or pure protein, and antibodies raised against either or both) is also used in direct or competition ELISAs (Enzyme-linked immunosorbent assay) (Rennard et al. Anal. Biochem. 104: 205–214, 1980). In a typical direct ELISA, a standard curve is established by binding a known concentration of peptide or pure protein (200 microliters) to the bottom of flat bottomed polyvinyl 96 well plates and serially diluting with Vollers buffer. The analyte is also bound at several different dilutions. The plate is incubated at 4° C. overnight, and then washed three times with phosphated buffered saline containing 0.054 a detergent such as TWEEN. The antibody raised against either the peptide or pure protein is used in either a direct (the antibody itself is tagged with a reporter molecule, which is usually an enzyme such as horseradish peroxidase, etc. ) or indirect procedure, and is diluted to an appropriate concentration with PBS+Tween, 200 microliters is added to each well, and the plate is incubated at room temperature ($\sim 22°-24°$ C.) for one hour. The plate is washed three times with PBS+Tween. If the antibody itself is tagged, the appropriate substrate (which will form a chromophore after it is acted on by the enzyme) is added, but if an indirect detection procedure is used, a second antibody (raised against the Ig fraction of the animal species used to elicit the first antibody, and tagged with a reporter) is diluted to an appropriate concentration and 200 microliters are added to each well. The plate is incubated for 1 hr at room temperature, and washed three times with PBS+TWEEN. The appropriate substrate for the reporter is then added. After the addition of substrate, the plate is incubated for 1–6 hrs, and terminated by addition of a color development inhibitor such that the resultant optical density values are within the linear range of the detection system. The amount of chromophore generated is determined by spectrophotometry, and the standard curve is determined by plotting the optical density vs. the amount of polypeptide or protein. The values for the analyte are determined from the standard curve.

In a typical competition ELISA, the antibody against a polypeptide or pure protein is diluted to an appropriate concentration and 100 microliter aliquots are first incubated in a round bottomed, non-adsorptive 96 well plate with different amounts of polypeptide or pure protein (to generate the standard curve), and the analyte at various dilutions (final volume). After incubation at 4° C. overnight, the aliquots are transferred to a 96 well flat-bottomed plate that has been previously treated by adsorbing a constant amount of polypeptide or antigen to the bottom of each well. The plates are then incubated, washed, etc. as described in the previous paragraph. The level of polypeptide or protein in an analyte is estimated from its ability to inhibit the binding of this antibody (which is either directly tagged with a reporter, or used in conjunction with a second antibody that is tagged) in comparison to the standard curve (which is generated by measuring the ability of known amounts of polypeptide or pure protein to competitively inhibit binding).

Immunohistochemistry with Antibodies Raised Against Intact Antibodies or Synthetic Peptides In this assay, antibodies (either monoclonal or polyclonal) raised against the invention (any synthetic polypeptide, or substantially pure protein preparation) are used to detect the localization (in a semi-quantitative fashion) within tissue sections (either frozen or fixed with an appropriate fixative) or cell culture preparations (either frozen or fixed). Tissue sections are processed and embedded in paraffin (for light microscopy) or Epon (or equivalent) (for electron microscopy) and sections of appropriate thickness are prepared. The specimen (either sections or cells) is prepared for immunohistochemistry by equilibrating in the physiological buffer and incubating with the antibody raised against the polypeptide or pure protein, diluted to an appropriate concentration. In cases of direct immunodetection, the specific antibody itself is covalently coupled to a reporter molecule (e.g., horseradish peroxidase, alkaline phosphatase, biotin or any other reporter). In cases of indirect immunodetection, a second antibody, raised against immunoglobulins derived from the animal species in which the specific antibody was elicited is covalently coupled to the reporter, and incubated with the specimen. After extensive washing the appropriate substrate for the reporter is added (e.g., diaminobenzidine as the substrate for horseradish peroxidase) and incubated for an appropriate amount of time relative to a positive control. The reaction is terminated, and the specimen is examined by light or electron microscopy and compared to a normal control specimen for evaluation (Timpl and Risteli. In Furthmayr, H. (ed) Immunochemistry of the Extracellular Matrix, Vol. 1 Boca Raton, CRC Press, 1982, pp.199–235; Bianco et al. In: Proceedings of the First Joint Meeting of the International Conference on Calcium Regulating Hormones and the American Society for Bone and Mineral Research, Elsevier Sci. Pub. Co., In Press ).

Use in Competition or Inhibition Assays, and Blocking of Biological Function

The invention (polypeptides or protein) is used in various competition assays as noted above for RIA and ELISA assays. Also they are used in inhibition of antibody localization in immunohistochemistry (a method of proof of specific antibody reaction) by first incubating the primary antibody with an excess amount of polypeptide or protein. The antibody is then incubated with the tissue sections or cells as described above. Blocking of the immunolocalization is indicative of specific reaction. In addition, polypeptides or protein are used to determine the presence or absence of an antibody in a test solution (e.g., patient's bodily fluids as In the case of pathological conditions such as autoimmunity, or in hybridoma growth medium or ascites fluid in the preparation of monoclonal antibodies).

The invention (polypeptides or protein) is used to either induce biological function, or to block it. In the case of cell attachment, the invention is adsorbed or crosslinked onto an inert support and used either in vivo or in vitro. The invention can be used to block cell attachment by incubating cells in suspension (or with a systemic delivery) which thereby inhibits reaction of cells with the substratum (e.g., Pierschbacher and Rouslahti, Nature #09: 30-34, 1984).

The Invention (anti-sense sequences derived from the cDNA or any derivative thereof (e.g., phosphorothioate, methylphosphonate, or in combination with targeting molecules) are used to block biological function by inhibition of protein synthesis. The anti-sense sequences are used in vivo by topical application or may be used systemically when covalently attached to a targeting agent that provides cell and tissue specific localization. vitro, they are used by addition to tissue culture medium, and are actively taken up by the cells, where they inhibit protein synthesis, thereby blocking biological function of the invention (Marcus-Sekura. Anal. Biochem. 172:289-295, 1988).

In situ Hybridization

The invention (anti-sense sequence of the cDNA) is used in in situ hybridization for the localization of mRNA within tissue sections and cell preparations. Typically, sections of tissues or cells (permeabilized by treatment either with detergent or Saponin) are fixed, embedded and sectioned as described above. Deparaffinized sections are pretreated under acid conditions prior to digestion with proteinase K, followed by acetylation with acetic anhydride in triethanolamine. The tagged (usually radiolabeled) anti-sense sequence (partial or full length) is added to the section in hybridization buffer and incubated overnight at 50° C., washed and treated with RNase to remove non-specifically bound probe, and then washed under increasingly stringent conditions. If the probe is radiolabeled, sections are subjected to autoradiography using Kodak NTB-2 emulsion. If the probe is tagged with another reporter, an appropriate detection system is used (Metsaranta et al. Calcif. Tiss. Int. 45: 146-152, 1989).

Northern Blot Analysis

The invention (antisense sequence derived from the cDNA) is used in Northern blot analysis to determine in a semi-quantitative fashion the presence of mRNA in extracts of tissues and cells. Total RNA is extracted and electrophoresed on formaldehyde agarose gels, and then transferred to nitrocellulose. The "Northern" blot is washed in prehybridization solution, and subsequently hybridization is carried out using a radiolabeled (or otherwise tagged) cDNA probe at 41° C. Then hybridization is visualized by standard autoradiography or any suitable detection system well known to one of ordinary skill in the art.

A diagnostic kit in accordance with the present invention which can be used in conjunction with RIA, ELISA, immunohistochemistry and the like, comprises separate containers containing:

a. An appropriate buffer for standards and samples.
b. A sample of the invention (polypeptide or protein) of known concentration.
c. A sample of antibody (either monoclonal or polyclonal) raised against the invention (polypeptide or protein) to be used at an appropriate dilution.
d. A buffer for the dilution of the antibody.
e. A sample of radiolabeled or otherwise tagged polypeptide or protein (the invention).
f. A solid bead or resion having a substrate covalently attached to it that will bind the specific antibody.
g. A sample of non-immune serum as a negative control, and instructional material for performing the test.

A bioassay in accordance with the present invention such as RIA, ELISA, immunohistochemistry and the like for detecting the level of certain human bond matrix proteins, comprises the steps of:

a. Preparing standards—The lyophilized polypeptide or protein of the present invention is resuspended in a buffer to yield a concentrated stock solution. The stock solution is diluted with buffer to yield standard solutions within a given range of protein or polypeptide concentration.
b. Preparing tubes for establishing the standard curve—In separate tubes, 100 microliters of each of the standard dilution samples is added along with 50 microliters of the antibody diluted in antibody buffer, and 50 microliters of radiolabeled polypeptide or pure protein.
c. Preparing tubes of samples to be analyzed—To separate tubes, add 50 microliters of buffer, 50 microliters of sample to be analyzed (at several different dilutions), 50 microliters of antibody diluted with antibody buffer, 50 microliters of radiolabeled polypeptide or pure protein.
d. Incubate at 4° C. overnight.
e. Add 50 microliters of solid support to capture the antibody-antigen complex. Incubate at 4° C. with constant agitation.
f. Centrifuge at 10,000× g for 5 min. Draw off supernatant, wash pellet with buffer and recentrifuge. Draw off supernatant.
g. Quantitate radioactivity of pellet.
h. Construct a standard curve by plotting the radioactivity in the standard tubes (y axis) vs. amounts (x axis).
i. Determine concentration of polypeptide or protein in the sample by placing the radioactivity on the curve at the appropriate y value and reading the corresponding x value (amount).

A probe in accordance with the present invention for detecting the presence of mRNA of certain bone matrix protein, comprises employing the anti-sense sequence derived from the cDNA sequence of said bone matrix protein as a probe.

A sequence for inhibiting protein synthesis comprises employing the anti-sense sequence of the cDNA (either partial or full length) and any chemically modified derivative of the cDNA sequences of the bone matrix protein of the present invention.

An antibody having specific binding affinity for the polypeptides of the present invention is easily made by conventional monoclonal or polyclonal techniques well known to one of ordinary skill in the art.

DEPOSIT

A deposit of the clones has been made at the ATCC, Rockville, Md., on Sep. 28, 1989, under the accession numbers as follows:

| | |
|---|---|
| B65g (bone sialoprotein/BSPII) | ATCC 40672 |
| HOP10I (BSPI/Osteopontin) | ATCC 40673 |
| P2 (Proteoglycan II/decorin) | ATCC 40674 |
| P16 (Proteoglycan I/biglycan) | ATCC 40675 |
| HON2 (osteonectin/sparc) | ATCC 40676 |
| OP12 (osteopontin 2) | ATCC 40677 |

The deposit shall be viably maintained, replacing if it becomes non-viable during the life of the patent, for a period of 30 years from the date of the deposit, or for 5 years from the last date of request for a sample of the deposit, whichever is longer, and upon issuance of the patent made available to the public without restriction in accordance with the provisions of the law. The Commissioner of Patents and Trademarks, upon request, shall have access to the deposit.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. An isolated cDNA having the nucleotide sequence shown in FIG. 1.

* * * * *